(12) United States Patent
Lockwood et al.

(10) Patent No.: US 7,903,827 B1
(45) Date of Patent: Mar. 8, 2011

(54) HEARING AID PROGRAMMING INTERFACE WITH CONFIGURATION ON DEMAND

(75) Inventors: Scott William Lockwood, West Jordan, UT (US); David Rex Scott, Sandy, UT (US)

(73) Assignee: Sonic Innovations, Inc., Salt Lake City, UT (US)

( * ) Notice: Subject to any disclaimer, the term of this patent is extended or adjusted under 35 U.S.C. 154(b) by 2094 days.

(21) Appl. No.: 10/824,761

(22) Filed: Apr. 13, 2004

(51) Int. Cl.
*H04R 29/00* (2006.01)
*H04R 25/00* (2006.01)
*A61B 5/00* (2006.01)
*A61B 5/12* (2006.01)

(52) U.S. Cl. .......... 381/60; 381/312; 381/314; 600/559; 73/585

(58) Field of Classification Search .............. 381/60, 381/312, 314, 315
See application file for complete search history.

(56) References Cited

U.S. PATENT DOCUMENTS

| | | | |
|---|---|---|---|
| 4,992,966 A | 2/1991 | Widin et al. | |
| 5,083,312 A | 1/1992 | Newton et al. | |
| 5,607,460 A | 3/1997 | Kroll et al. | |
| 6,359,992 B1 | 3/2002 | Preves et al. | |
| 6,366,863 B1 | 4/2002 | Bye et al. | |
| 6,389,142 B1 | 5/2002 | Hagen et al. | |
| 6,424,722 B1 | 7/2002 | Hagen et al. | |
| 6,442,279 B1 | 8/2002 | Preves et al. | |
| 6,449,662 B1 | 9/2002 | Armitage | |
| 6,647,345 B2 | 11/2003 | Bye et al. | |
| 2001/0009019 A1 | 7/2001 | Armitage | |
| 2002/0015506 A1 | 2/2002 | Aceti et al. | |
| 2002/0054689 A1* | 5/2002 | Zhang et al. | 381/312 |
| 2002/0083235 A1 | 6/2002 | Armitage | |
| 2002/0111745 A1 | 8/2002 | Bye et al. | |
| 2002/0168075 A1* | 11/2002 | Hagen et al. | 381/312 |
| 2002/0191805 A1 | 12/2002 | Hagen et al. | |
| 2003/0014566 A1 | 1/2003 | Armitage | |
| 2003/0059073 A1 | 3/2003 | Bren et al. | |
| 2005/0283263 A1* | 12/2005 | Eaton et al. | 700/94 |

FOREIGN PATENT DOCUMENTS

| | | |
|---|---|---|
| CA | 2223660 | 12/1997 |
| CA | 2343986 | 9/1999 |
| CA | 2371909 | 8/2000 |
| WO | WO 0154458 A2 * | 7/2001 |
| WO | WO0169969 | 9/2001 |

* cited by examiner

*Primary Examiner* — Brian Ensey
*Assistant Examiner* — Sunita Joshi
(74) *Attorney, Agent, or Firm* — Holland & Hart

(57) ABSTRACT

In accordance with the present invention the hearing aid programmer includes a program memory for receiving firmware programming instructions and a parameter memory for receiving patient-specific hearing aid parameters to be programmed into a coupled programmable hearing aid. A software hearing aid fitting system executed on a computer such as a PC provides the parameters. In response to a user command, the computer causes a firmware program (selected from one or more firmware programs stored on the computer) appropriate to the hearing aid to be programmed to be downloaded to the programmer.

13 Claims, 3 Drawing Sheets

HEARING AID PROGRAMMING INTERFACE WITH CONFIGURATION ON DEMAND

FIELD OF THE INVENTION

The present invention relates generally to the field of hearing aids and more particularly to the field of programmable hearing aids. More particularly, it relates to the configuration of an interface device used to permit a computer such as a personal computer (PC) to program user-specific settings into a programmable hearing aid.

BACKGROUND OF THE INVENTION

In the hearing aid industry a number of hearing aid manufacturers manufacture hearing aids. These hearing aids all differ in various ways. Modern hearing aids employ programmable technologies such as programmable digital signal processors. Manufacturers typically sell their hearing aids to vendors such as audiologists (sometimes termed "dispensers") who, in turn, sell the hearing aids to end users (patients). Since one dispenser may need to be able to provide patients with the hearing aids of a number of different manufacturers, yet the dispenser may want to have a single computer dedicated to the effort of programming hearing aids, rather than one computer dedicated per vendor supported, a generic hearing aid interface (referred to as a "hearing aid programmer") is commonly used to connect programmable hearing aids to the computer so that they may be programmed with parameters from the computer which are specifically matched to the hearing loss of the patient. The hearing aid programmer must be configured to provide the specific commands and the electrical interface required by the hearing aid(s) being programmed. The configuration process takes time and must provide the correct setup for the hearing aid(s) being programmed. When the hearing aid programmer is connected to the computer, the hearing aids(s) to be programmed may not be known and generally won't be connected to the hearing aid programmer until after the hearing aid programmer is connected to the computer. If the hearing aid programmer is configured at this time (power-up), the configuration may or may not be correct when actual hearing aids are connected and the fitting system software running on the computer is executed. It may be that the configuration will have to be cleared out and a new configuration entered into the hearing aid programmer. This can be wasteful and inefficient as the time taken to perform these processes is usually not insignificant.

Some hearing aid programmers are designed to trigger a configuration sequence when they are attached to the computer. This power-up sequence automatically loads firmware into the hearing aid programmer to configure it for communicating with particular hearing aids. Later, when the manufacturer-specific fitting system software is executed on the computer and generates the patient-specific parameters to be stored in the hearing aid, it may turn out that the hearing aid configuration in the hearing aid programmer is incorrect or incomplete for the specific hearing aid(s) to be programmed at that time.

What is needed is a solution which provides the ability to configure the hearing aid programmer's interface characteristics just prior to the time that the hearing aids are to be configured.

BRIEF DESCRIPTION OF THE INVENTION

In accordance with the present invention the hearing aid programmer includes a program memory for receiving firmware programming instructions and a parameter memory for receiving patient-specific hearing aid parameters to be programmed into a coupled programmable hearing aid. A software hearing aid fitting system executed on a computer such as a personal computer (PC) provides the parameters. In response to a user command, the computer causes a firmware program (selected from one or more firmware programs stored on the computer) appropriate to the hearing aid to be programmed to be downloaded to the hearing aid programmer.

BRIEF DESCRIPTION OF THE DRAWINGS

The accompanying drawings, which are incorporated into and constitute a part of this specification, illustrate one or more embodiments of the present invention and, together with the detailed description, serve to explain the principles and implementations of the invention.

In the drawings.

DETAILED DESCRIPTION

Embodiments of the present invention are described herein in the context of a hearing aid programming system. Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention as illustrated in the accompanying drawings. The same reference indicators will be used throughout the drawings and the following detailed description to refer to the same or like parts.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

In accordance with the present invention, the components, process steps, and/or data structures may be implemented using various types of operating systems, computing platforms, computer programs, and/or general purpose machines. In addition, those of ordinary skill in the art will recognize that devices of a less general purpose nature, such as hardwired devices, field programmable gate arrays (FPGAs), application specific integrated circuits (ASICs), or the like, may also be used without departing from the scope and spirit of the inventive concepts disclosed herein.

Figure 1:
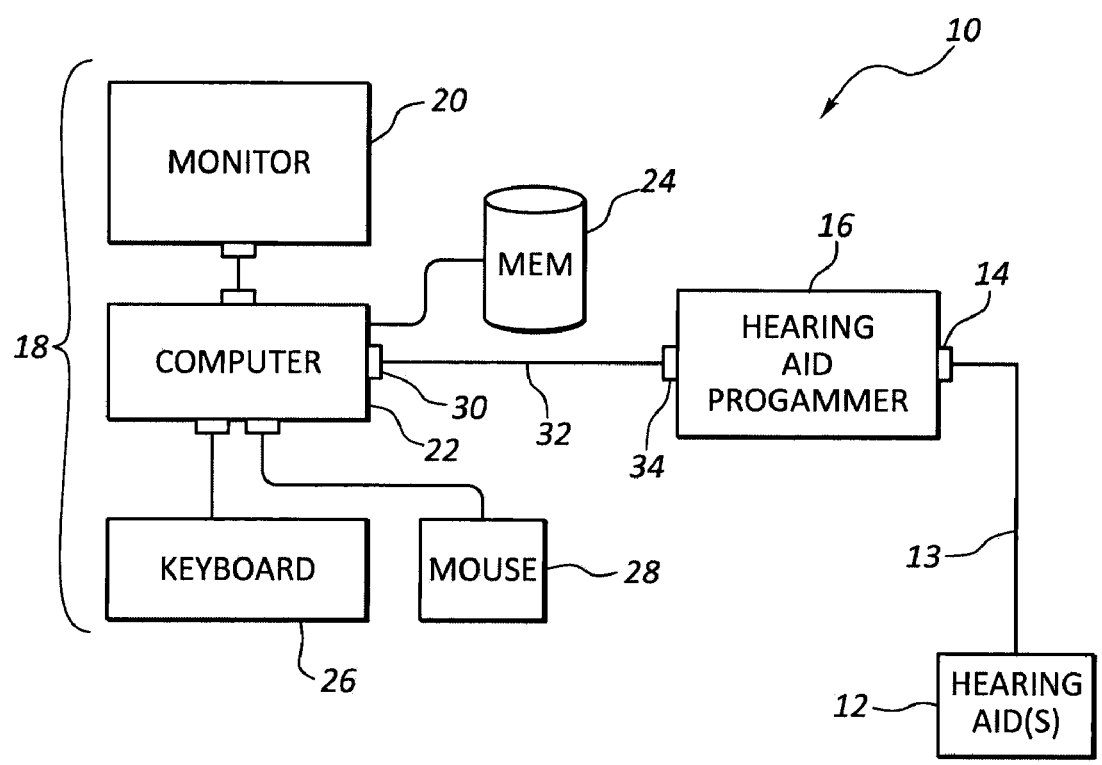
FIG. 1 is a system block diagram of a hearing aid programming system.

Turning now to FIG. 1 a hearing aid programming system 10 is illustrated in block diagram form. One or more hearing aids 12 are coupled over coupling 13 to the hearing aid interface 14 of a hearing aid programmer 16. The interface between hearing aid programmer 16 and hearing aid(s) 12 includes hearing aid interface 14 of hearing aid programmer 16, coupling 13 between interface 14 and hearing aid(s) 12 and interface circuitry (not shown) which is incorporated into all programmable hearing aids 12. The coupling may be by any convenient means such as wire, coaxial cable, one or more twisted pairs of conductors, cable, fiber-optic cable, wireless connection (e.g., blue tooth, IEEE 802.11, Universal Serial Bus, Firewire, and the like), and other conventional data transmission mechanisms.

A computer 18, such as a personal computer (PC) or other convenient data processor for executing hearing aid fitting software programs, typically includes a monitor 20 for providing a visual output to an operator, a computer system unit 22 containing a microprocessor and other related circuitry, a memory 24 which may be of any form including optical, electronic and magnetic, a keyboard 26 and a mouse 28 for user input. Computer 18 may be alternatively a server or main frame type of computer, a desktop type of computer, a laptop type of computer, a PDA (personal data assistant) type of computer, or the like.

Computer 18 includes an output port 30 for outputting signals over coupling 32 to computer interface 34 of hearing aid programmer 16.

The interface between computer 18 and hearing aid programmer 16 includes port 30 of computer 18, coupling 32 and computer interface 34 of hearing aid programmer 16. This interface may be of any conventional or proprietary type suitable to meet the data transmission requirements. For example, the Universal Serial Bus 1.0, 1.1 and 2.0 standard interfaces are well known to those of ordinary skill in the art, provide a high data transmission rate, and are quite suitable for this application. The IEEE 1394 series of "Firewire" interface standards is similarly suitable as are various parallel and serial data interface standards well known to those of ordinary skill in the art.

Figure 2:
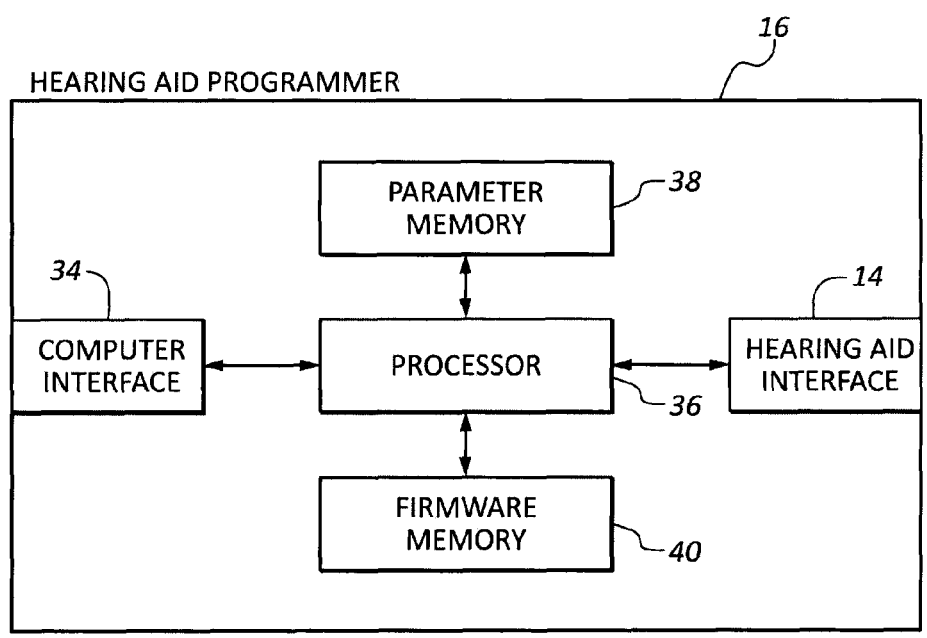
FIG. 2 is a block diagram of a hearing aid programmer.

Turning now to FIG. 2, a block diagram of a hearing aid programmer 16 is shown. A processor 36 coupled to parameter memory 38 and firmware memory 40 receives instructions and data from computer 18 via computer interface 34. Parameters such as an individual's settings to be programmed into one or more hearing aids 12 are stored in parameter memory 38. Instructions for interfacing with and programming hearing aids 12 are stored in firmware memory 40. These memories may be of any type such as electronic, optical and magnetic, and if electronic may be of the nonvolatile type (e.g., EEPROM (electrically erasable programmable ROM), EPROM (electrically programmable ROM), FLASH (a type of EEPROM), PROM (programmable ROM), SRAM (static random access memory), ROM (read only memory) and the like) or volatile type (e.g., RAM (random access memory), DRAM (dynamic RAM) and the like).

The processor executes the instructions in firmware memory in response to signaling from the computer 18 and uses the data stored in parameter memory 38 to generate instructions to program hearing aids 12 which instructions are output over hearing aid interface 14 to the hearing aid(s) 12.

Figure 3:
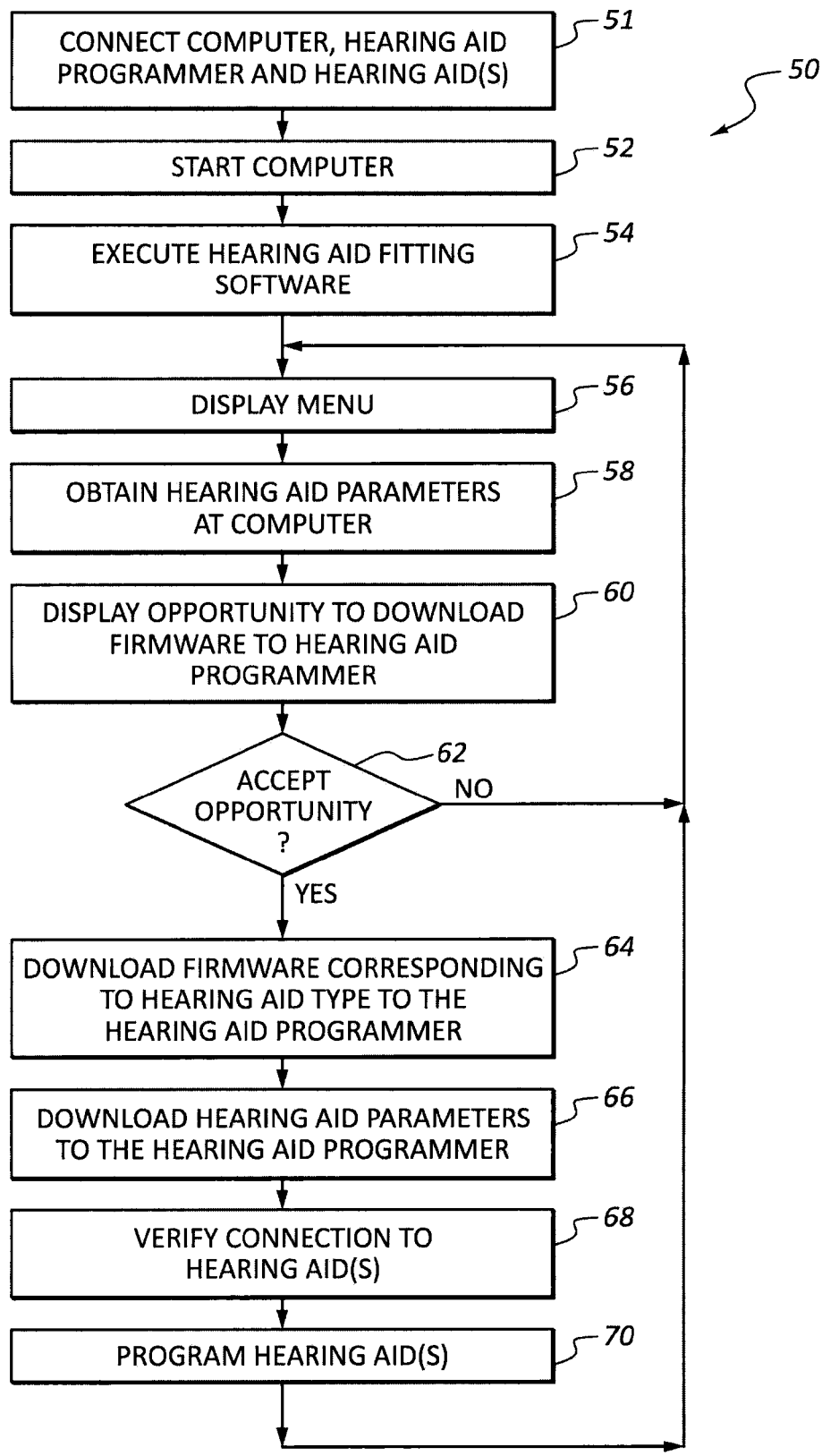
FIG. 3 is a flow chart of a method for programming a hearing aid using a programmable hearing aid programmer.

Turning now to FIG. 3 a flowchart of a method 50 of programming one or more hearing aids 12 is shown.

At block 51 the computer 18, hearing aid programmer 16 and hearing aid(s) 12 to be programmed are all properly coupled or connected together. This coupling does not need to occur precisely at this point in the process but the hearing aid programmer 16 and the computer 18 should be connected before they attempt to communicate with one another and likewise the hearing aid programmer 16 and the hearing aid(s) 12 to be programmed should be connected before they attempt to communicate with one another.

At block 52 the computer 18 is booted or initiated ("started") as is well understood by those of ordinary skill in the art.

At block 54 hearing aid fitting software is executed on computer 18. Hearing aid fitting software is typically provided by programmable hearing aid manufacturers and is typically specific to a particular model, line or brand of hearing aids. At block 56 the fitting software displays a menu of options on the monitor 20. The dispenser may now select desired option such as downloading information to the hearing aid(s). The fitting software allows the dispenser of the hearing aids to either enter into the computer predetermined parameters specific to the patient, or, in conjunction with hearing testing equipment, allows such parameters to be captured directly at computer 18 (or another device) while testing a patient.

At block 58 the parameters relating to a particular patient are obtained by one means or another at the computer 18.

At block 60, once the parameters are available, the opportunity to download firmware appropriate to the programmer (and hearing aids) is displayed to the dispenser. This may be done visually over the monitor 20 or audibly over speakers (not shown) or in any other conventional or convenient manner. This opportunity may be indicated in a manner that does not specifically explain to the dispenser that firmware will now be downloaded, e.g., the message "Continue?" or the like may be displayed.

At block 62 the dispenser must select whether or not to download firmware to the hearing aid programmer 16. If the firmware is not to be downloaded at this point, control branches back to block 56. If the firmware is to be downloaded, control branches to block 64. Again, this response could be as simple as responding "Y" or "N" to the query "Continue?" described above.

At block 64 firmware corresponding to the hearing aid programmer and hearing aid is downloaded to hearing aid programmer 16. The correct firmware (typically one firmware program or one of a plurality of different firmware programs) may be selected manually at the computer by the dispenser or automatically by having the computer 18 query the hearing aid programmer 16 for an identification and having the hearing aid programmer 16 query the hearing aid(s) 12 for an identification. The requests of these queries may then be used to select the appropriate firmware program.

At block 66 the parameters associated with the patient for whom the hearing aid(s) 12 are being programmed is downloaded from the computer 18 to the hearing aid programmer 16.

Optionally, at block 68 the connection to hearing aid(s) 12 is verified. This step may be performed earlier and it's position in FIG. 3 between blocks 66 and 70 should not be read to define a necessary order or to limit the scope of the claims appended hereto.

At block 70 the hearing aid(s) 12 are programmed by the hearing aid programmer 16 in a conventional manner well known to those of ordinary skill in the art. This will typically involve writing information to nonvolatile memory in hearing aid(s) 12. Control then branches to block 56.

In accordance with one embodiment of the present invention, on power-up, the hearing aid programmer 16 may be set into a neutral configuration that will not damage any hearing aid(s) 12 that may be attached. This will typically involve disallowing high-voltage programming signals from being sent from the hearing aid coupling to the hearing aid (or causing the hearing aid to generate same) prior to verifying the exact type of hearing aid(s) 12 that are attached.

Accordingly, a delayed hardware configuration scheme that is triggered by the fitting system software has been shown and described In accordance with the invention no manufacturer specific firmware is downloaded to the hearing aid programmer 16 immediately upon power-up or upon being connected to computer 18. Later, when the fitting system software for a particular manufacturer is executed on computer 18, the proper firmware to support hearing aids from that manufacturer or specific to the attached hearing aid is downloaded to hearing aid programmer 16 and thus hearing aid programmer 16 is properly configured. Subsequently, parameters relating specifically to the patient are downloaded to hearing aid programmer 16.

In this manner a more efficient system is realized that avoids downloading firmware to hearing aid programmer 16 that may not be correct for the hearing aids that are eventually to be programmed.

While embodiments and applications of this invention have been shown and described, it would be apparent to those skilled in the art having the benefit of this disclosure that many more modifications than mentioned above are possible without departing from the inventive concepts herein. The invention, therefore, is not to be restricted except in the spirit of the appended claims.

What is claimed is:

1. A method for programming a programmable hearing aid with a configurable hearing aid programmer under the control of a computer, the method comprising:
   starting the computer;
   executing hearing aid fitting software on the computer;
   obtaining hearing aid fitting parameters at the computer;
   displaying the opportunity to download a firmware program to the hearing aid programmer in response to the execution of the hearing aid fitting software on the computer;
   downloading a firmware program to the hearing aid programmer in response to an affirmative response to said displaying, wherein the firmware program configures the hearing aid programmer to communicate with the programmable hearing aid;
   downloading hearing aid parameters to the hearing aid programmer; and
   programming the programmable hearing aid with the hearing aid programmer.

2. The method of claim 1, further comprising:
   verifying that a connection between the hearing aid programmer and the hearing aid exists prior to said programming.

3. The method of claim 1, further comprising:
   coupling the computer to the hearing aid programmer prior to said displaying.

4. The method of claim 1, further comprising:
   coupling the hearing aid to the hearing aid programmer prior to said downloading hearing aid parameters.

5. The method of claim 3, further comprising:
   coupling the hearing aid to the hearing aid programmer prior to the said downloading hearing aid parameters.

6. A hearing aid programming system, comprising:
   a computer under the control of hearing aid fitting software;
   a hearing aid programmer coupled to the computer and responsive to a firmware program, the firmware program downloadable to the hearing aid programmer only in response to an execution of the hearing aid fitting software on the computer and a user input at the computer, wherein the firmware program configures the hearing aid programmer to communicate with a programmable hearing aid;
   the programmable hearing aid coupled to the hearing aid programmer, the hearing aid programmable with parameters transmitted from the computer to the hearing aid programmer and programmed into nonvolatile memory of the programmable hearing aid by the hearing aid programmer.

7. The hearing aid programming system of claim 6, further comprising:
   a parameter memory associated with the hearing aid programmer for receiving and storing the parameters.

8. The hearing aid programming system of claim 7, further comprising:
   a firmware memory associated with the hearing aid programmer for receiving and storing the firmware program.

9. The hearing aid programming system of claim 8, further comprising:
   a computer interface for providing an electrical and data communications interface between the computer and the hearing aid programmer.

10. The hearing aid programming system of claim 9, further comprising:
    a hearing aid interface for providing an electrical and data communications interface between the hearing aid programmer and the hearing aid.

11. The hearing aid programming system of claim 10, wherein:
    the computer interface complies with the Universal Serial Bus 1.0, 1.1 and 2.0 standard protocol.

12. Apparatus for programming a hearing aid, comprising:
    computer means for executing hearing aid fitting software and capturing patient-specific parameters;
    hearing aid programmer means responsive to said computer means and to a firmware program for receiving parameters from said computer means and programming the parameters into the hearing aid, wherein the firmware program downloads to the computer means in response to the execution of the hearing aid fitting software by the computer means, wherein the firmware program configures the hearing aid programmer means to communicate with the hearing aid; and
    user interface means for obtaining a command from a user prior to downloading the firmware program from said computer means to said hearing aid programmer means.

13. A program storage device readable by a machine, tangibly embodying a program of instructions executable by the machine to perform a method for programming a programmable hearing aid with a configurable hearing aid programmer comprising:
    starting the computer;
    executing hearing aid fitting software on the computer;
    obtaining hearing aid fitting parameters at the computer;
    displaying the opportunity to download a firmware program to the hearing aid programmer in response to the execution of the hearing aid fitting software on the computer;
    downloading the firmware program to the hearing aid programmer in response to an affirmative response to said displaying, wherein the firmware program configures the hearing aid programmer to communicate with the programmable hearing aid;
    downloading hearing aid parameters to the hearing aid programmer; and
    programming the programmable hearing aid with the hearing aid programmer.

* * * * *